Dec. 19, 1967 J. M. GARABEDIAN Plant Pat. 2,783
PLUM TREE
Filed Oct. 13, 1966
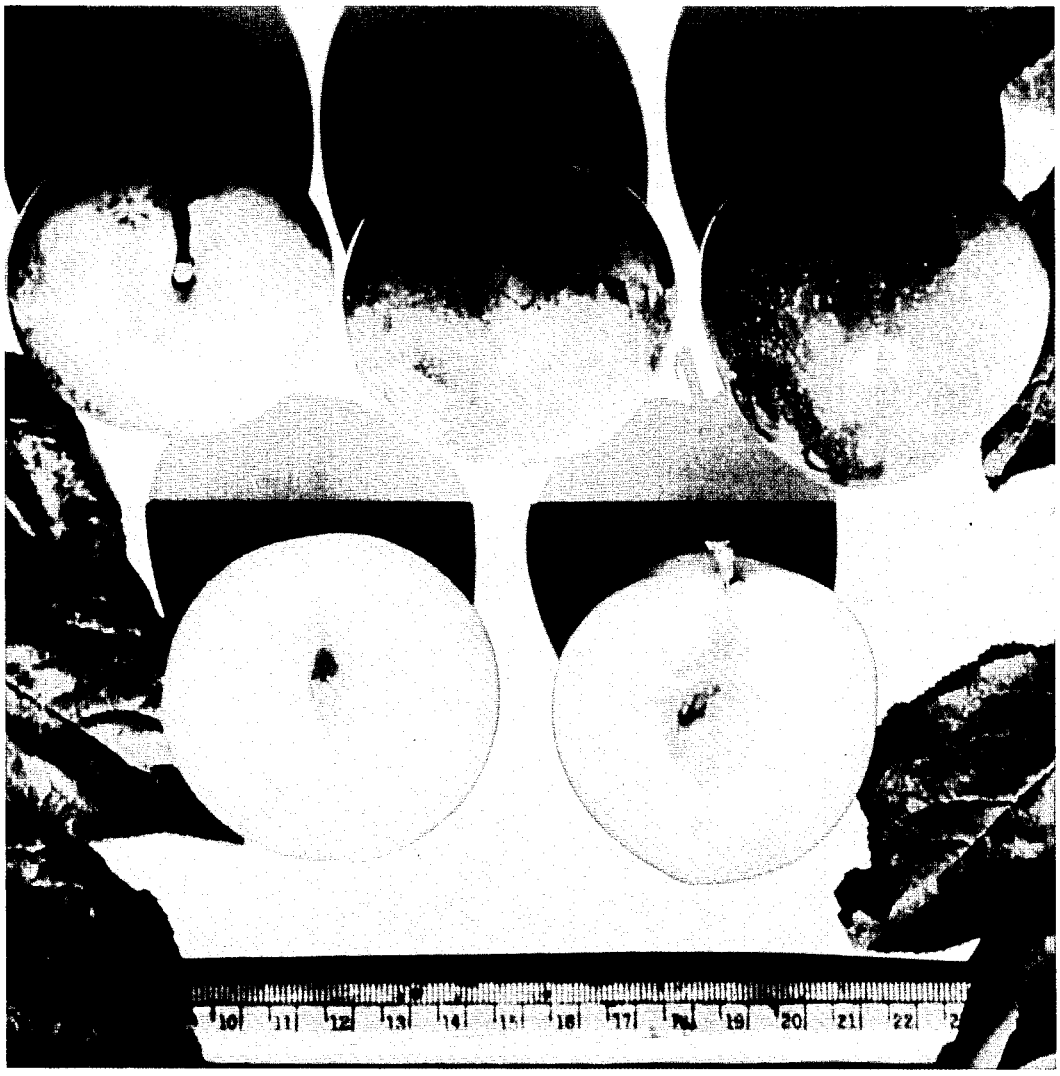
INVENTOR
John M. Garabedian
BY
Webster & Webster
ATTORNEYS

United States Patent Office

Plant Pat. 2,783
Patented Dec. 19, 1967

2,783
PLUM TREE

John M. Garabedian, Fresno, Calif., assignor to Peach & Willow Farms, Fresno, Calif., a corporation of California

Filed Oct. 13, 1966, Ser. No. 586,580
1 Claim. (Cl. Plt.—38)

This invention relates to a new and distinct variety of plum tree which is a regular and productive bearer of large, yellow flesh, clingstone fruit having yellow-green skin partially overspread with a bright pinkish red.

The tree and its fruit have general resemblance to the Laroda (unpatented) variety of plum and which is the presumed pollen parent, but in specific comparison the fruit of the instant variety is distinctively characterized by a harvest period about ten days later, by a somewhat different form, and by a brighter red overcolor on the skin.

The herein claimed variety of plum tree was originated by me in the following manner:

Seeds were gathered from trees of the El Dorado (unpatented) plum in an orchard located on my ranch in Madera County, Calif.; such trees of the El Dorado plum growing side by side with trees of the Laroda plum. The seeds, as thus gathered, were planted in a nursery plot located on my ranch in Fresno County, Calif.; the resultant seedlings—from open pollinated El Dorado—having been maintained under close observation by me. One of such seedlings evidenced distinctive characteristics which made it desirable for commercial growing, and such seedlings—which is the present variety—was, therefore, selected by me for asexual reproduction.

I accomplished asexual reproduction of the variety by buds thereof top-worked on mature nectarine trees in an orchard located on the aforesaid ranch in Fresno County, Calif.; all of such reproductions having run true to the original tree in all respects.

The drawing is an illustration, by photographic reproduction in color, of fruit of the variety together with leaves thereof; the view including two cut halves to expose the flesh.

Referring now more specifically to the pomological details of this new and distinct variety of plum tree, the following is an outline description thereof; all major color plate identifications being by reference to Maerz and Paul Dictionary of Color, except where common terms of color definition are employed.

Tree:
- *Size.*—Large.
- *Vigor.*—Vigorous.
- *Growth.*—Upright.
- *Density.*—Dense.
- *Form.*—Vase shaped.
- *Hardiness.*—Hardy.
- *Production.*—Productive.
- *Bearing.*—Regular bearer.

Trunk:
- *Size.*—Stocky.
- *Texture.*—Medium.

Branches:
- *Size.*—Medium.
- *Texture.*—Medium.
- *Color.*—Dorsal side—Garland Green (22–G–7). Ventral side—Metallic Green (15–L–6).
- *Lenticels.*—Number—medium to few—mostly on new wood. Size—small. Texture—on older wood—many vertical striations.

Leaves:
- *Size.*—Medium. Average length—3½"–4½". Average width—1½"–1⅞. (Above from 1966 growth—center of tree.)
- *Form.*—Some elliptical; some oval; many oblanceolate.
- *Leaf base.*—Mostly broadly acute; some obtuse.
- *Leaf apex.*—Acutely pointed—many cuspidate.
- *Thickness.*—Medium.
- *Leaf veins.*—Pinnately net veined.
- *Margin.*—Glandular; crenate.
- *Petiole.*—Length—medium, 5/16"–⅝", mostly ½". Size—medium. Color: dorsal side—Box Green (22–L–3) to Reddish Green (7–H–9); ventral side—Leek Green (22–K–5) to Light Yellow-Green (14–L–2).
- *Glands.*—Average number—2 (range 0–3). Usually alternate; medium size; globose; red; positioned on petiole and base of blade.
- *Stipules.*—Usually 2 (range 0–2).
- *Leaf buds.*—Small; pointed.

Flower buds:
- *Hardiness.*—Hardy.
- *Size.*—Small.
- *Length.*—Short.
- *Form.*—Plump; free.
- *Surface.*—Glabrous.
- *Set.*—Medium to light. Few buds, usually 2 (sometimes 3) on short spurs. Most buds formed laterally on one-year wood.

Flowers:
- *Blooming period.*—Date of first bloom—Mar. 4, 1966. Date of full bloom—Mar. 10, 1966. Medium, as compared with other varieties.
- *Size.*—Small, usually 17 to 18 mm. across open flower. Petals usually small. Petical averages 7 mm. in length.
- *Color.*—White.

Fruit:
- *Maturity when described.*—Hard ripe.
- *Date of first picking.*—July 10, 1966.
- *Date of last picking.*—July 27, 1966.
- *Size.*—Very uniform; large. Average diameter axially—2¼". Average transversely in suture plane—2⅛".
- *Form.*—Very uniform; symmetrical. Round ovate—globose.
- *Suture.*—An inconspicuous line to distinct; shallow; extends from base to beyond but discontinues at apex.
- *Ventral surface.*—Rounded slightly.
- *Lips.*—Usually equal.
- *Cavity.*—Circular. Very small, with suture showing on one side. Average depth—⅛". Average breadth—⅜". Markings—yellowish.
- *Base.*—Rounded to truncate.
- *Apex.*—Short; rounded; mostly pointed.
- *Pistil point.*—Apical.
- *Stem.*—Medium length; holds tight; very little brush. Average length—½". Average width—3/16".

Skin:
- *Thickness.*—Thick.
- *Texture.*—Tough; slightly astringent; bitter.
- *Tenacity.*—Tenacious to flesh.
- *Tendency to crack.*—None in dry season.
- *Down.*—None.
- *Color.*—Yellow-Green (11–L–4) undercolor, sometimes shading in part to 11–H–9; such undercolor being partially overspread with a Bright Pinkish Red (47–L–1). Light blue-gray bloom. Small round light yellowish dots submerged near apex, irregularly larger near base, and very few at stem ends.

Flesh:

*Amygdalin.*—Scant to wanting.
*Juice.*—Moderate.
*Texture.*—Usually firm—some medium. Fine; crisp; melting.
*Fibers.*—Very few, usually none noticeable.
*Ripens.*—Evenly.
*Flavor.*—Delicate to vinous.
*Aroma.*—Wanting.
*Eating quality.*—Best; very pleasant.
*Color.*—Yellow (12–K–4).

Stone:

*Type.*—Cling; adheres to flesh over entire surface.
*Size.*—Large. Average length—1". Average breadth —9/16". Average thickness—5/16".
*Form.*—Obovoid; necked.
*Base.*—Straight. Average width—1/8"–3/16".
*Apex.*—Acuminate.
*Sides.*—Equal.
*Surface.*—Irregularly furrowed and ridged near base.
*Pits.*—None.
*Ventral edge.*—Thin, with wing toward base.
*Dorsal edge.*—Narrow, with shallow narrow groove toward base.
*Kernel.*—Elliptical; very slight amygdalin taste; viable.

*Seed coat.*—Pellicle—brown. Amygdalin—very slight.
*Tendency to split.*—None.
*Color.*—Rattan (11–K–6).

Use: Market—local. Dessert.
Keeping quality: Good.
Shipping quality: Good.

The plum tree and its fruit herein described may vary in slight detail due to climatic and soil conditions under which the variety may be grown; the present description being of the variety as grown in the Central Valley of California.

The following is claimed:

A new and distinct variety of plum tree, substantially as illustrated and described, which is a regular and productive bearer of large, yellow flesh, clingstone fruit having yellow-green skin partially overspread with a bright pinkish red; characterized by general resemblance in tree and fruit to the Laroda plum but specifically distinct therefrom by a harvest period which is about ten days later.

No references cited.

ROBERT E. BAGWILL, *Primary Examiner.*